United States Patent [19]

Rossall

[11] Patent Number: 5,061,495

[45] Date of Patent: Oct. 29, 1991

[54] ANTIBIOTIC DERIVED FROM B. SUBTILIS

[75] Inventor: Stephen Rossall, Kegworth, England

[73] Assignee: Agricultural Genetics Company Limited, Cambridge, England

[21] Appl. No.: 319,759

[22] Filed: Mar. 7, 1989

[30] Foreign Application Priority Data

Mar. 7, 1988 [GB] United Kingdom ................ 8805394

[51] Int. Cl.$^5$ ...................... A61K 35/74; C12P 21/02; C12N 1/20
[52] U.S. Cl. .................................. 424/520; 435/70.1; 435/71.3; 435/252.5; 530/825
[58] Field of Search .................. 435/71.3, 70.1, 252.5; 424/95, 520; 530/825

[56] References Cited

U.S. PATENT DOCUMENTS

| | | | |
|---|---|---|---|
| 2,895,882 | 7/1959 | Thorne et al. | 530/825 |
| 3,687,926 | 8/1972 | Arima et al. | 530/825 |
| 3,940,479 | 2/1976 | Shomura et al. | 435/71.3 |
| 4,181,714 | 1/1980 | Misato et al. | 435/71.3 |

FOREIGN PATENT DOCUMENTS 276132 7/1988 European Pat. Off. .............. 424/93
2508766 1/1983 France ................................. 435/71.3

OTHER PUBLICATIONS

Vater, Chem. Abstracts, vol. 106 (1987) 29811h.
Peypoux et al., J. Antibiotics, vol. 39, No. 5, (1986) pp. 636–641.
Peypoux et al., J. Antibiotics, vol. 32, No. 2, (1979) pp. 136–140.
Journal of Phytopathology, vol. 115, 1986, pp. 204–213, Loeffler et al., "Antifungal Effects of Bacilysin and Fengymycin from Bacillus . . . ".

*Primary Examiner*—Jacqueline Stone
*Attorney, Agent, or Firm*—Oblon, Spivak, McClelland, Maier & Neustadt

[57] ABSTRACT

The invention provides a novel antibiotic or antibiotic fraction and a process for producing it by culturing a suitable microorganism. Among other defined properties, the antibiotic has a protein and lipid content, a molecular weight of about 63,500 daltons and antibiotic activity against fungi and gram-positive bacteria, but not against gram-negative bacteria. It is useful for plant protection.

14 Claims, No Drawings

ANTIBIOTIC DERIVED FROM B. SUBTILIS

This invention relates to an antibiotic which is derivable from Bacillus subtilis strains NCIB 12375, 12376 and 12616, and related strains.

The properties of B. subtilis strains NCIB 12375, 12376 and 12616 are described in European Patent Application Publication No. 0 276 132. These strains were deposited on 22 Dec. 1986 (NCIB 12375 and 12376) and on 24 Dec. 1987 (NCIB 12616) at The National Collections of Industrial and Marine Bacteria Ltd. (NCIB), Torry Research Station, P.O. Box 31, 135 Abbey Road, Aberdeen, AB9 8DG, Scotland.

We have found that the antifungal properties of B. subtilis strains NCIB 12375, 12376 and 12616 are associated with a novel antibiotic.

Antibiotics produced by strains of Bacillus species have been previously reported (ref.1). Where these have been characterised they have typically been found to be small peptides and peptidolipids of molecular weight in the range 270–4,500 daltons. There is one example of an antibiotic of size greater than 100,000 daltons being produced by a strain (APPL-1) of B. subtilis (ref.3) although a subsequent paper claims a size of 5–10,000 (ref.2). Most Bacillus antibiotics are active against gram-positive bacteria but a small number have been found to have activity against gram-negative bacteria, yeasts or fungi (ref.4).

All previously reported antifungal antibiotics produced by B.subtilis strains belong to one of three groups based on location of the antibiotic (inside or outside of the microbial cell) and structure of the molecule (refs 5–7). These groups are as follows: intracellular cyclic peptidolipids, extracellular cyclic peptidolipids, extracellular cyclic peptides. With the exception noted above, all of these antibiotics are of a size less than 4,500 daltons. The previously reported antifungal antibiotics produced by B.subtilis strains are summarised in Table 1.

TABLE 1

| Antifungal Antibiotics Produced by B. subtilis strains | | |
|---|---|---|
| Type of Compound | Name | Reference |
| Intracellular cyclic peptidolipids | Mycosubtilin | 8 |
| Extracellular cyclic peptidolipids | Aspergillus factor | 9 |
| | Bacillomycin A | 10 |
| | Bacillomycin B | 11 |
| | Bacillomycin D | 12 |
| | Bacillomycin F | 13 |
| | Bacillomycin L | 14 |
| | Bacillomycin R | 15 |
| | Bacillomycin S | 16 |
| | Eumycin | 17 |
| | Fengycin | 18 |
| | Iturin A | 12 |
| | Toximycin | 19 |
| Extracellular cyclic peptides | Chaetomacin | 20 |
| | Fungistatin | 21 |
| | Mycobacillin | 22 |
| | Rhizoctonia factor | 9 |

Physical properties of some of the antibiotics listed in Table 1 have been reported. The iturin group of antibiotics are insoluble in water, and some are soluble in acetone (refs. 5,6 and 12). Iturin A and bacillomycin F have been shown to be neutral peptidolipids by electrophoresis (ref. 12). Iturin A and bacillomycin L are thermostable at pH 3 and pH 10, but not at any other pH values (refs. 5, 14 and 23). Bacillomycin L does not partition into butanol at neutral pH (ref.24). The intracellular peptidolipid, mycosubtilin, is insoluble in methanol, ethanol and butanol (refs. 5 and 8).

Mycobacillin and chaetomacin are both soluble in acetone but the former is insoluble in water at pH values of 7 and below (refs. 20 and 22). Rhizoctonia factor is insoluble in ethanol and butanol, and is thermostable only at pH 2 (refs. 5 and 9). Fungistatin is an amphoteric peptide which forms an inactive gel when contacted with water (ref.10).

An active fraction containing a mixture of anti-fungal antibiotics can be isolated from cultures of B.subtilis strain B-3 (ref.25). The antibiotic mixture gives a positive reaction to the ninhydrin test for protein. The mixture is thermostable only at pH values of less than 5.0, which may be related to the observation that the mixture is insoluble in water at pH values of less than 7.5. The mixture is soluble in ethanol, methanol and isopropanol, but not in ethyl acetate, acetone, diethyl ether or methylene dichloride.

A antibiotic faction isolated from cultures of B.subtilis strain APPL-I was thermostable, and was composed of 95% protein and 5% carbohydrate (ref.2).

The fatty acid composition of the lipid component of the antibiotics iturin A, fengycin and bacillomycin F and L, has been characterised (refs.18,26–28). The fatty acids are methyl branched, contain from 13 to 16 carbon atoms and, with the exception of fengycin, are constituents of B-amino acids.

The present invention provides a novel antibiotic derivable from Bacillus subtilis strains NCIB, 12375, 12376 and 12616, and which has properties distinct from previously reported antibiotics produced by B.subtilis strains. The antibiotic of the present invention has the following characteristics:

(1) Antibiotic activity against fungi and gram-positive bacteria, but not against gram-negative bacteria:
(2) A molecular weight of 63,500±3,700 daltons as determined by gel filtration chromatography which is calibrated against globular protein standards;
(3) A positive reaction to the following tests for the presence of protein: Lowry, absorbance of light of wavelength 280 nm, biuret and ninhydrin.
(4) A protein content comprising of the amino acids aspartic acid, threonine, serine, glutamic acid, proline, alanine, valine, isoleucine, leucine and tyrosine;
(5) A protein content which is resistant to digestion by the enzyme pronase E;
(6) A lipid content comprising fatty acids containing from 14 to 17 carbon atoms;
(7) An optimum pH of 6.0–7.0;
(8) Retention of activity when held at 110° C. for 10 minutes over the pH range 5.0–9.0;
(9) Soluble in water at pH values greater than 5.0;
(10) Soluble in methanol, ethanol and butanol, and partially soluble in dimethylsulphoxide; and
(11) Insoluble in acetone, petroleum ether, chloroform, toluene and hexane.

B.subtilis NCIB 12376 was derived from B.subtilis NCIB 12375. A mutant or derivative of NCIB 12375 also capable of producing the antibiotic is strain NCIB 12616. Both NCIB 12376 and NCIB 12616 can be regarded as antibiotic-producing related strains of NCIB 12375. It will be recognised by those skilled in the art that other strains of B.subtilis, and other species of microorganism may be found to produce the antibiotic that is the subject of the present invention.

The antibiotic may be used for the protection of plants against fungal diseases. Cultures of microorganisms producing the antibiotic may be used directly by spraying liquid cultures onto plant foliage in order to protect against foliar fungal diseases. In some cases it may be more efficaceous to use antibiotic fractions from suitable cultures, rather than whole culture broths. Such fractions may contain spores of the microorganism.

Many plants have foliage on which it is difficult to achieve good dispersion and adhesion of plant protection agents; in such cases it is advantageous to formulate cultures or antibiotic fractions with components that aid dispersion and adhesion. Suitable formulants will be known to those skilled in the art.

The antibiotic may also be used for the protection of plants against soil-borne fungal diseases. Cultures of antibiotic-producing microorganisms, or antibiotic fractions derived therefrom, can be used to coat seeds in order to confer protection against soil-borne diseases. Alternatively, cultures, or antibiotic fractions, may be applied directly to the soil in the vicinity of seeds. Liquid or solid formulations may be used for this purpose.

The invention is illustrated by the following examples.

EXAMPLE 1

Purification of the Antibiotic

The bacterium *B.subtilis* NCIB 12376 was grown in a liquid medium at 30° C. in an orbital shaker for 72 hours. One of the following two chemically defined growth media was used:

| Medium 1 | | | |
|---|---|---|---|
| Glucose | 10 g | FeSO$_4$ | 0.01 g |
| KH$_2$PO$_4$ | 2.0 g | Glutamic acid | 5 g |
| MgSO$_4$ | 0.5 g | Water 1 liter | |
| KCl | 0.5 g | | |
| MnCl$_2$ | 0.01 g | | |
| Medium 2 | | | |
| Sorbitol | 20 g | FeSO$_4$ | 0.01 g |
| KH$_2$PO$_4$ | 1.0 g | Glutamic acid | 2.5 g |
| MgSO$_4$ | 0.5 g | Asparagine | 2.5 g |
| KCl | 0.5 g | Water 1 liter | |
| MnCl$_2$ | 0.01 g | | |

Bacterial cells and spores were removed from the broth by centrifugation at 10,000 g for 20 minutes and the cell-free medium treated with HCl to reduce the pH to 2.0. The antibiotic precipitated out and was collected by further high-speed centrifugation. The resultant pellet was redissolved in a small volume of 0.1M NaOH, further water added and the pH lowered to 8.0. This aqueous preparation was partitioned three times with an equal volume of butanol until antibiotic activity could only be detected in the organic phase.

The organic phases were then bulked and evaporated to dryness at 40° C. in-vacuo using a rotary evaporator. The antibiotic-containing residue was redissolved in potassium phosphate buffer pH 6.0. Gel filtration chromatography was performed using Sephadex G100 columns (Sephadex is a Trade Mark) of 50 ml volume. After the column had been equilbriated with two column volumes of 0.25M sodium phosphate buffer pH 7.0, 0.5 ml of partially purified antibiotic was applied to the top of the column. The column was eluted with 0.25M sodium phosphate buffer pH 7.0 and 1.5 ml fractions were collected with a LKB 7000 fraction collector. Fractions were assayed for antibiotic activity as described in Example 3.

Antibiotic activity was detected only in fractions 11 to 14. Calibration of the column with molecular weight markers (the globular proteins, bovine serum albumen, egg albumen, chymotrypsin and cytochrome c) demonstrated that the antibiotic has a molecular weight of 63,500±3,700 daltons. Calibration with linear dextrans indicated that the antibiotic has a molecular weight of 35,000 daltons. No antibiotic activity was found in fractions corresponding to a molecular weight of less than 4,500 daltons nor was any activity found in the void volume where molecules of size greater than 100,000 daltons would be located.

When Medium 1 was used for growth of the bacterium, the gel filtration fraction with antibiotic activity was found to contain protein, lipid and carbohydrate (1.2 mg/ml). When Medium 2 was used for growth of the bacterium the antibiotic fraction had a considerably reduced carbohydrate content (0.1 mg/ml) but there was no concomitant decrease in antibiotic activity. This suggests that the antibiotic is composed of protein and lipid components.

EXAMPLE 2

Purification of the Antibiotic by Fast Protein Liquid Chromatography (FPLC)

An antibiotic-containing fraction was prepared from a glucose-grown culture of *B.subtilis* NCIB 12376 as described in Example 1. The fraction was treated with pronase E, as described in Example 6, in order to digest any proteins susceptible to proteolysis. Protein-containing components of the fraction were separated by anion exchange FPLC on a 5 ml Q Seph FF column (supplied by Pharmacia). 100 μl of the fraction were loaded onto the column and eluted (1 ml per minute) with 20 mM Tris buffer pH 8.0 and a gradient of NaCl (starting concentration zero, final concentration 1M, total volume of gradlent 56 ml). A 254 nm detector (0.45 AU sensitivity was used). Four peaks were detected. The four fractions were each dialysed against a 1000-fold excess of distilled water and then concentrated two-fold by evaporation in vacuo. The dialysed fractions were then assayed for antibiotic activity as described in Example 3. Antibiotic activity was found only in the fourth fraction to be eluted from the column.

EXAMPLE 3

Bioassay for Antibiotic Activity

Diffusion bioassays were performed in glass dishes containing a lawn of assaymicroorganism on agar, and assay samples were applied to wells cut in the agar. Diffusion of the antibiotic creates zones of inhibition of growth of the assay organism, where the diameter of the zone is approximately proportional to the logarithm of antibiotic concentration. Thus, antibiotic activity can be quantified.

Prior to use, glass bioassay dishes (20×20 cm) were washed with methylated spirit and then filled with 200 ml of molten Sabouraud's glucose agar which was allowed to set and form a base layer.

*Botrytis cinerea* conidial suspensions were prepared by adding approximately 20 ml sterile distilled water to a flask containing a sporulating solid culture of *B. cinerea*. Conidia were dislodged by scraping with a sterile wire loop and the resulting suspension filtered through sterile medium. The filtrate was then collected and spores washed twice with sterile distilled water following centrifugation at 2000 g for 3 minutes. The concentration of conidia was estimated by haemocytometer counts and adjusted to $1 \times 10^5$ per ml by dilution with sterile distilled water. 10 ml of this suspension was added to 100 ml cooled (40° C.) molten Sabouraud's glucose agar. This seeded agar was poured over the base layer and left to solidify. Wells were cut in both layers of agar with a No. 4 core borer, using a template of 6 rows with 6 wells per row.

100 μl aliquots of solutions to be assayed were dispensed into the wells, with at least 3 replicate samples of each solution per plate. Aqueous solutions for bioassay were first passed through a 0.45 μm membrane filter. Dishes were covered and incubated at 18° C. for 3 days.

When incubation was complete, the diameters of inhibition zones were measured with a pair of calipers. Zones were visualised by flooding the dishes with aqueous trypan blue for 1 minute and then briefly washing with tap water.

EXAMPLE 4

Presence of Protein in the Antibiotic

An antibiotic-containing fraction was prepared from a glucose-grown culture of *B.subtilis* NCIB 12376 as described in Example 1. The fraction was tested and found to be positive for protein by the following methods: Lowry, biuret, ninhydrin and absorbance of light of wavelength 280 nm. The Lowry, biuret and ninhydrin assays were performed as described in the literature (refs. 29-31). The absorbance of light of wavelength 280 nm was measured in a spectrophotometer.

EXAMPLE 5

Amino Acid Composition of the Antibiotic

An antibiotic-containing fraction was prepared from a glucose-grown culture of *B.subtilis* NCIB 12376 as described in Example 1. The fraction was acid-digested by adding hydrochloric acid to a concentration of 5.75M and incubating under nitrogen for 4 hours at 100° C. The digested sample was concentrated by evaporation, resuspended in water and adjusted to neutral pH with NaOH. The amino acid content was determined on a LKB 4400 amino acid analyser using a $250 \times 4$ mm Aminex A9 resin column and a standard lithium citrate buffer elution system.

There are 10 major peaks attributable to amino acids. The molar ratios of these are given in Table 2. There are also five other major peaks which do not correspond to any of the common proteinaceous amino acids. The identity of the compounds corresponding to these peaks is unknown.

EXAMPLE 6

Resistance to Digestion by Pronase E

An antibiotic-containing fraction was prepared from a glucose-grown culture of *B.subtilis* NCIB 12376 as described in Example 1. The fraction was incubated in 0.25M sodium phosphate buffer pH 7.5 containing 1 mg pronase E for 3 hours at 20° C. Pronase E was then inactivated by boiling the sample for 10 minutes. The sample was partitioned into butanol as described in Example 1. Both the aqueous and organic fractions were assayed for antibiotic activity as described in Example 3; activity was found only in the organic fraction which was then evaporated to dryness in vacuo. The solid was redissolved in a small volume of 1M NaOH and adjusted to pH 7 with HCl. The solution was subjected to gel filtration chromatography on a Sephadex G-100 column as described in Example 1. Fractions corresponding to a molecular weight of 63,500 daltons were pooled and adjusted to pH 2 with 1M HCl to precipitate the antibiotic. Bioassay as described in Example 3 confirmed that antibiotic activity was present. The precipitate was redissolved as described above. The sample was acid-digested and the amino acid content determined as described in Example 5. Treatment with pronase E did not significantly alter the molar ratio of amino acids (Table 2), indicating that the antibiotic is resistant to digestion by this protease.

TABLE 2

| Amino acid composition of the antibiotic | | |
|---|---|---|
| | Molar Ratio* | |
| Amino Acid | Untreated | Pronase Treated |
| Aspartic acid | 5.1 | 7.0 |
| Threonine | 1.8 | 2.2 |
| Serine | 2.1 | 2.8 |
| Glutamic acid | 8.0 | 8.2 |
| Proline | 1.4 | 1.5 |
| Alanine | 1.0 | 1.0 |
| Valine | 3.4 | 4.1 |
| Isoleucine | 1.1 | 1.1 |
| Leucine | 6.2 | 3.7 |
| Tyrosine | 4.4 | 1.5 |

*compared to alanine

EXAMPLE 7

Fatty Acid Composition of the Antibiotic

An antibiotic-containing fraction was prepared from a glucose-grown culture of *B.subtilis* NCIB 12376 as described in Example 1. The fraction was saponified by incubating with 5% sulphuric acid in dry methanol for 2 hours at 72° C. The saponified sample was extracted with octanol and the fatty acid content of the extract analysed by gas chromatography/mass spectrometry (GC/MS) on a Hewlett Packard GC/MS system fitted with a 24 meter BP20 fused silica capillary column. Seven major peaks were detected and found to correspond to the fatty acids listed in Table 3. The fatty acids range in chain length from 14 to 17 carbon atoms and all are apparently fully saturated. Three of the fatty acids are thought to contain methyl side chains but the positions of the branch points are unknown. The saponification method used will hydrolyse ester bonds but is unlikely to break peptide bonds. It is therefore most likely that the fatty acids are linked to the protein component of the antibiotic by ester bonds. Thus they are not constituents of B-amino acids as is the case with most antibiotics isolated from other strains of *B.subtilis*.

TABLE 3

| Fatty acid composition of the antibiotic | |
|---|---|
| Fatty Acid | % of total |
| 14:0 | 7 |
| 15:0 | 9 |
| 15:0 (methyl branched) | 36 |
| 16:0 | 23 |
| 16:0 (methyl branched) | 4 |
| 17:0 | 6 |
| 17:0 (methyl branched) | 15 |

EXAMPLE 8

Thermostability of the Antibiotic

*B.subtilis* NCIB 12375 was grown in a yeast peptone-glucose broth at 30° C. in an orbital shaker for 72 hours.

Bacterial cells and spores were removed from the broth by centrifugation at 10,000 g for 20 minutes. Aliquots of culture broth were adjusted by the addition of either dilute HCl or dilute NaOH to pH values over the range 4–10. A portion of each sample was then dispensed into 5 McCartney bottles and autoclaved at 110° C. for 10 minutes. After cooling, samples were bioassayed for antibiotic activity as described in Example 3. Activity was lost on heating at pH 4.0 and pH 10.0 but retained over the pH range 5.0–9.0 (see Table 4).

TABLE 4

The effect of pH on the thermal stability of the antibiotic

| pH | Antibiotic Activity* |
|---|---|
| 4.0 | 0 |
| 5.0 | 11.8 |
| 6.0 | 17.8 |
| 7.0 | 19.6 |
| 8.0 | 19.6 |
| 9.0 | 16.0 |
| 10.0 | 0 |

*mean diameter (mm) of zone of inhibition of B. cinerea

EXAMPLE 9

Optimum pH for Antibiotic Activity

Culture broths of B.subtilis NCIB 12375 were prepared and adjusted to pH values over the range 4.0–10.0 as described in Example 8. Samples were passed through 0.45 μm membrane filters prior to bioassay as described in Example 3. The optimum pH for antibiotic activity is pH 6.0–7.0 (see Table 5). At pH values of 5.0 or less, the antibiotic precipitated out of solution.

TABLE 5

Optimum pH for antibiotic activity

| pH | Antibiotic Activity* |
|---|---|
| 4.0 | 8.0 |
| 5.0 | 12.0 |
| 6.0 | 21.8 |
| 7.0 | 21.8 |
| 8.0 | 18.8 |
| 9.0 | 18.8 |
| 10.0 | 17.8 |

*mean diameter (mm) of zone of inhibition of B. cinerea

EXAMPLE 10

Solubility of the Antibiotic

B.subtilis NCIB 12375 was grown in growth medium 1 of Example 1, supplemented with 5 g L-glutamic acid, at 30° C. in an orbital shaker for 72 h. The broth was harvested and the antibiotic extracted by acid precipitation an butanol partitioning as described in Example 1. 10 ml aliquots of the butanol extract were evaporated to dryness in vacuo at 40° C., and the residue washed three times with 10 ml of solvent (see Table 4 for solvents used). The solvent washings were bulked before evaporation in-vacuo. This solvent extract was redissolved in 1 ml potassium phosphate buffer pH 6.0. The remains of the washed extract were also redissolved in 1 ml buffer. Samples were bioassayed for antibiotic activity as described in Example 3 (see Table 6).

TABLE 6

Solubility of the antibiotic

| Solvent | Solvent | Antibiotic Activity* Undissolved Residue |
|---|---|---|
| Sterile distilled water | 17.3 | 0 |
| Methanol | 17.8 | 0 |
| Ethanol | 17.0 | 0 |
| Butanol | 14.8 | 10.0 |
| Dimethylsulphoxide | 15.5 | 11.5 |
| Acetone | 0 | 17.0 |
| Petroleum ether | 0 | 16.3 |
| Chloroform | 0 | 16.5 |
| Toluene | 0 | 16.3 |
| Hexane | 0 | 14.5 |

*mean diameter (mm) of zone of inhibition of B. cinerea

The antibiotic is soluble in water, methanol, ethanol and butanol, partially soluble in dimethylsuphoxide, and insoluble in acetone, petroleum ether, chloroform, toluene and hexane.

EXAMPLE 11

Comparison of in vitro Antibiotic Activity of B.subtilis NCIB 12375 with other B.subtilis Strains The antibiotic activity of B.subtilis NCIB 12375 was compared with that of B.subtilis NCIB 8872 (a known producer of bacillomycin L) and B.subtilis BD-1 (a known producer of iturin A) in in vitro tests.

All three strains were grown in a yeast peptone-glucose broth, or the glucose minimal medium described in Example 1, at 30° C. in an orbital shaker for 72 hours. Bacterial cells and spores were removed from the broths by centrifugation at 10,000 g for 20 minutes. The cell-free broths were bioassayed against Penicillium chrysogenum using the well-diffusion assay described in Example 3. Two types of agar were used: Sabouraud's glucose agar and V8 juice agar. The latter consisted of 200 ml V8 juice (Campbell's Soup Ltd.), 800 ml of distilled water and 20 g of Oxoid agar No. 3. The results are shown in Table 7.

TABLE 7

Comparison of in vitro activity of antibiotics from three B. subtilis strains

| Liquid Growth Medium | Agar Bioassay Substrate | Diamter of Zone of Inhibition (cm)* | | |
|---|---|---|---|---|
| | | NCIB 12375 | NCIB 8872 | BD-1 |
| Yeast peptone | V8 | 1.93 | 1.40 | 2.43 |
| | Sabouraud | 1.83 | 1.27 | 2.50 |
| Glucose minimal | V8 | 2.00 | 1.86 | 2.46 |
| | Sabouraud | 2.60 | 2.60 | 2.80 |

*mean of 6 replicate diffusion wells

In vitro activity of the antibiotic from B.subtilis NCIB 12375 was intermediate to that of bacillomycin L and iturin A in this assay. Attempts were made to compare activities against Botrytis fabae, Gauemannomyces graminis and Fusarium oxysporum using a pre-inoculated plate technique. All antibiotics were active against all three fungi but quantification was impossible due to marked differences in morphology of microbial growth.

EXAMPLE 12

Comparison of in vivo Antibiotic Activity of B.subtilis NCIB 12376 with other B.subtilis Strains In vitro assessment of antibiotic activity as described in Example 11 is somewhat artificial; more realistic data can be obtained from in vivo tests.

B.subtilis strains NCIB 12376, NCIB 8872 and BD-1 were grown in a yeast peptone-glucose broth at 30° C. in an orbital shaker for 72 hours. The broths were tested in vivo against *Botrytis fabae* as follows. For each *B.subtilis* strain, 12 bifoliate leaves were detached from faba beans at the four leaf growth stage and sprayed with broth to run-off. Controls were sprayed with water. Leaves were air-dried at room temperature. Each leaf was challenged with 25 15 µl drops of water containing $10^5$ *B.fabae* spores per ml. Leaves were incubated at 20° C. in light and the number of disease lesions scored (see Table 8). Equivalent levels of disease control by each antibiotic was observed 4 days after inoculation, but by 5 days the antibiotic from *B.subtilis* NCIB 12376 was demonstrating superior disease control activity.

TABLE 8

Comparison of in vivo activity of antibiotics from three *B. subtilis* strains

| B. subtilis strain | % of Inoculation Sites With No Disease Lesions | |
|---|---|---|
| | 4 days | 5 days |
| Control | 4 | 0 |
| NCIB 12376 | 52 | 49 |
| NCIB 8872 | 58 | 42 |
| BD-1 | 51 | 38 |

EXAMPLE 13

Use of Formulated Antibiotic-Containing Cultures of *B.subtilis* for Control of Wheat Powdery Mildew

*B.subtilis* NCIB 12376 was grown in a yeast peptone-glucose broth at 30° C. in an orbital shaker for 72 hours. The formulants listed in Table 9 were added to samples of culture broths at the concentrations given in Table 9 and stirred until dispersed or dissolved. The formulated broths were tested for control of wheat powdery mildew (*Erysiphe graminis*) by spraying to run-off wheat plants (cv. Aquila) at the two leaf stage (Zadocks GS 12) prior to inoculation with an aqueous suspension of *E. graminis* conidia. For each formulation 20 replicate pots of plants were sprayed. Ten pots from each treatment were then thoroughly drenched with a mist bench for 4 minutes, one hour after spraying. All pots were incubated in a glasshouse for 14 days before assessment of disease levels (Table 9). The results indicate that formulated culture broths reduce disease levels of plants, and in some cases exert disease control comparable to that of the commercial fungicide triadimefon. Disease control by culture broths was seen even on drenched plants, indicating that formulants can minimise wash-off of the control agent.

TABLE 9

Use of formulated antibiotic-containing cultures of *B. subtilis* NCIB 12376 for control of wheat powdery mildew.

| Treatment | Disease Level (% leaf area infected) | |
|---|---|---|
| | Undrenched | Drenched |
| No treatment | 2.0 | 5.6 |
| Triadimefon (2 g · $1^{-1}$) | 0.2 | 0.1 |
| Formulated cultures: | | |
| 0.025% Silwett L77 | 0.6 | 1.2 |
| 2.0% Ashlade adjuvant oil | 0.1 | 0.4 |
| 2.0% Chiltern Cropspray 11E | 0.3 | 0.2 |
| 2.0% Sprayprover | 0.3 | 0.2 |
| 0.1% Bond | 0.8 | 1.5 |
| 0.1% Sprayfast | 1.0 | 1.2 |
| 1.0% Wilt-Pruf S-600 | 1.0 | 1.0 |

REFERENCES

1. Berdy, J. (1974). Advances in Applied Microbiology, 18, 308-406.
2. Baker, C. J. et al. (1983). Phytopathology, 73, 1148-1152.
3. Baker, C. J. and Stavely, J. R. U.S. Pat. No. 4,582,704.
4. Katz, E. & Demain, A. L. (1977). Bacteriological Reviews, 41, 449-474.
5. Sharon, N. et al. (1954). Nature, 174, 1190-1191.
6. Besson, F. et al. (1976). Journal of Antibiotics, 29, 1043-1049.
7. Besson, F. et al. (1978). Journal of Antibiotics, 31, 284-288.
8. Walton, R. B. & Woodruff, H. B. (1949). Journal of Clinical Investigations, 28, 924-926.
9. Michener, H. D. & Snell, N. (1949). Archives of Biochemistry, 22, 208-214.
10. Cercos, A. P. (1950). Rev. Invest. Agric., 4, 325-335.
11. Shibasaki, I. & Terui, G. J. (1954). Journal of Fermentation Technology, 32, 115-118.
12. Peypoux, F. et al. (1980). Journal of Antibiotics, 33, 1146-1149.
13. Michel, G. et al. (1983). Fermentation and Bioindustrial Chemistry, 16, 19.
14. Landy, M. et al, (1948). Proceedings of the Society of Experimental Biology, New York, 67, 539.
15. Babad, J. et al, (1952). Nature, 170, 618-619.
16. Esterhuizen, B. (1974). Aspects of the action of bacillomycin S. Ph.D. Thesis, University of Stellenbosch.
17. Johnson, E. A. & Burdon, K. L. (1946). Journal of Bacteriology, 51, 591.
18. Vanittanokom, N. & Loeffler, W. (1986). Journal of Antibiotics, 39 888-901.
19. Stessel, G. L. et al, (1953). Mycologia, 45, 325-334.
20. Tautorus, T. E. & Townsley, P. M. (1984). Applied Environmental Microbioloyy, 47, 775-779.
21. Hobby, G. L. et al. (1949). Journal of Clinical Investigations, 28, 927-933.
22. Majumdar, S. K. & Bose, S. K. (1958). Nature, 181, 134-135.
23. Delcambe, L. (1965). Bull Soc. Chim. Belg., 74, 315-328.
24. Barr, J. G. (1976). Journal of Applied Bacteriology, 39, 1-13.
25. McKeen, C. D. et al. (1986). Phytopathology, 76, 136-139.
26. Peypoux, F. et al. (1973). Tetrahedron, 29, 3455-3459.
27. Mhammedi, A. et al. (1982). Journal of Antibiotics, 35,306-311.
28. Peypoux, F. et al. (1978). Biochemistry, 17, 3992-3996.
29 (1951). Journal of Biological Chemistry, 193, 265.
30. (1949). Journal of Biological Chemistry, 177, 751.
31. (1948). Journal of Biological Chemistry, 176, 367.

I claim:
1. An antibiotic or antibiotic fraction having the following characteristics:
   (1) antibiotic activity against fungi and gram-positive bacteria, but not against gram-negative bacteria;
   (2) a molecular weight of 63,500±3,700 daltons as determined by gel filtration chromatography which is calibrated against globular protein standards;

(3) a positive reaction to the following tests for the presence of protein: Lowry, absorbance of light of wavelength 280 nm, biuret and ninhydrin;

(4) a protein content comprising the amino acids aspartic acid, threonine, serine, glutamic acid, proline, alanine, valine, isoleucine, leucine and tyrosine;

(5) a protein content which is resistant to digestion by the enzyme pronase E;

(6) a lipid content comprising fatty acids containing from 14 to 17 carbon atoms;

(7) an optimum pH of 6.0-7.0;

(8) retention of activity when held at 110° C. for 10 minutes over the pH range 5.0 to 9.0;

(9) soluble in water at pH values greater than 5.0;

(10) soluble in methanol, ethanol and butanol, and partially soluble in dimethylsulphoxide: and

(11) insoluble in acetone, petroleum ether, chloroform, toluene and hexane.

2. An antibiotic or antibiotic fraction according to claim 1, which is derived from a microorganism of the genus Bacillus.

3. An antibiotic or antibiotic fraction according to claim 2, which is derived from a strain of *Bacillus subtilis*.

4. An antibiotic or antibiotic fraction according to claim 3, which is derived from *Bacillus subtilis* strain NCIB 12375, 12376 or 12616, or an antibiotic-producing derivative or mutant thereof.

5. An antibiotic fraction derivable from *Bacillus subtilis* NCIB 12376 or an antibiotic-producing related strain and having the following characteristics:

(a) a molecular weight in the range 35000 to 63000 daltons;

(b) a positive reaction to the protein tests: Lowry, extinction at 280 nm, biuret and ninhydrin;

(c) the protein content is resistant to digestion by pronase E; and (d) a lipid content comprising $C_{14}$-$C_{17}$ fatty acids.

6. An antibiotic fraction according to claim 5, in which the protein fraction has an amino acid content as given hereinbefore in Table 2.

7. An antibiotic fraction according to claim 5 or 6, in which the lipid fraction has a fatty acid composition as given hereinbefore in Table 3.

8. A process for producing an antibiotic or antibiotic fraction having the following characteristics:

(1) antibiotic activity against fungi and gram-positive bacteria, but not against gram-negative bacteria;

(2) a molecular weight of $63,500 \pm 3,700$ daltons as determined by gel filtration chromatography which is calibrated against globular protein standards;

(3) a positive reaction to the following tests for the presence of protein: Lowry, absorbance of light of wavelength 280 nm, biuret and ninhydrin;

(4) a protein content comprising the amino acids aspartic acid, threonine, serine, glutamic acid, proline, alanine, valine, isoleucine, leucine and tyrosine;

(5) a protein content which is resistant to digestion by the enzyme pronase E;

(6) a lipid content comprising fatty acids containing from 14 to 17 carbon atoms;

(7) an optimum pH of 6.0-7.0;

(8) retention of activity when held at 110° C. for 10 minutes over the pH range 5.0 to 9.0;

(9) soluble in water at pH values greater than 5.0;

(10) soluble in methanol, ethanol and butanol, and partially soluble in dimethylsulphoxide; and

(11) insoluble in acetone, petroleum ether, chloroform, toluene and hexane, which comprises culturing a microorganism capable of producing the antibiotic, and recovering the antibiotic from the culture.

9. A process according to claim 8, wherein the microorganism is of the genus Bacillus.

10. A process according to claim 9, wherein the microorganim is a strain of *Bacillus subtilis*.

11. A process according to claim 10, wherein the microorganism is *Bacillus subtilis* strain NCIB 12375, 12376 or 12616, or an antibiotic-producing derivative or mutant thereof.

12. A process according to any of claims 8 to 11, wherein cells of the microorganism are removed from the culture, and the resulting cell-free medium is acidified to cause the antibiotic to precipitate.

13. A process according to any of claims 8 to 12, wherein the microorganism is cultured until spore-forming cells predominate over vegetative cells and spores and antibiotic have accumulated in the culture, the pH is reduced to precipitate the antibiotic, and the solid phase is separated from the liquid phase whereby a mixture of spores and antibiotic is recovered.

14. A plant protection composition comprising an antibiotic or antibiotic fraction according to any of claims 1 to 7, and a carrier or diluent therefor.

* * * * *